US011465346B2

(12) United States Patent
Li et al.

(10) Patent No.: US 11,465,346 B2
(45) Date of Patent: *Oct. 11, 2022

(54) BIOPRINTER SPRAY HEAD ASSEMBLY AND BIOPRINTER

(71) Applicant: REVOTEK CO., LTD, Sichuan (CN)

(72) Inventors: Yijun Li, Chengdu (CN); Deming Wang, Chengdu (CN); Leqing Zhang, Chengdu (CN); Xuemin Wen, Chengdu (CN)

(73) Assignee: Revotek Co., Ltd, Sichuan (CN)

( * ) Notice: Subject to any disclaimer, the term of this patent is extended or adjusted under 35 U.S.C. 154(b) by 1092 days.

This patent is subject to a terminal disclaimer.

(21) Appl. No.: 16/067,532

(22) PCT Filed: Dec. 30, 2015

(86) PCT No.: PCT/CN2015/099806
§ 371 (c)(1),
(2) Date: Jun. 29, 2018

(87) PCT Pub. No.: WO2017/113161
PCT Pub. Date: Jul. 6, 2017

(65) Prior Publication Data
US 2021/0162660 A1    Jun. 3, 2021

(51) Int. Cl.
*B29C 64/209*    (2017.01)
*B33Y 30/00*    (2015.01)
*B29C 64/112*    (2017.01)

(52) U.S. Cl.
CPC .......... *B29C 64/209* (2017.08); *B29C 64/112* (2017.08); *B33Y 30/00* (2014.12)

(58) Field of Classification Search
CPC ......... A61F 2002/30985; B05B 7/0012; B05B 7/0408; B29C 64/106; B29C 64/112;
(Continued)

(56) References Cited

FOREIGN PATENT DOCUMENTS

| CN | 101107167 A | 1/2008 |
| CN | 103009812 A | 4/2013 |

(Continued)

OTHER PUBLICATIONS

Extended European Search Report dated Jul. 26, 2019 in connection with EP Application No. 15911790.2.

(Continued)

*Primary Examiner* — Manley L Cummins, IV
(74) *Attorney, Agent, or Firm* — Wolf, Greenfield & Sacks, P.C.

(57) ABSTRACT

The present disclosure provides a bioprinter spray head assembly and a bioprinter, wherein the spray head assembly is internally provided with a first flow channel and a second flow channel, an outlet of the first flow channel is adjacent to an outlet of the second flow channel, and the outlet of the second flow channel is configured to make a second material sprayed therefrom move towards a first material out of the outlet of the first flow channel, such that the second material sprayed from the outlet of the second flow channel and the first material sprayed from the outlet of the first flow channel are combined together to form a fluid printing unit. The bioprinter spray head assembly can guide the auxiliary materials to wrap the cells for protection, thereby reducing the cell damage caused by the extrusion pressure and the frictional force subjected in the printing process, so as to improve the survival rate of the cells and present a high reliability.

7 Claims, 2 Drawing Sheets

(58) Field of Classification Search
CPC ....... B29C 64/209; B33Y 30/00; B33Y 40/00; B41J 2/1433; B41J 2002/14475; C12M 1/00

See application file for complete search history.

(56) References Cited

FOREIGN PATENT DOCUMENTS

| | | | |
|---|---|---|---|
| CN | 104441654 A | | 3/2015 |
| CN | 105125316 A | | 12/2015 |
| CN | 105167879 A | | 12/2015 |
| CN | 204839829 U | | 12/2015 |
| CN | 105167879 | * | 8/2017 |
| DE | 10 2006 017595 A1 | | 10/2007 |
| JP | 2008-522814 A | | 7/2008 |
| WO | WO 2006/065978 A2 | | 6/2006 |
| WO | WO 2014/197999 A1 | | 6/2014 |
| WO | WO 2014/197999 A1 | | 12/2014 |
| WO | WO 2015/077262 A1 | | 5/2015 |
| WO | WO 2015065936 | * | 7/2015 |

OTHER PUBLICATIONS

International Search Report and Written Opinion for PCT/CN2015/099806, dated Sep. 22, 2016.
International Preliminary Report on Patentability for PCT/CN2015/099806, dated Jul. 3, 2018.
Communication Pursuant to Article 94(3) EPC for European Application No. EP 15911790.2, dated Dec. 16, 2020.
Japanese Office Action dated Sep. 3, 2019 in connection with JP Application No. 2018-534168.

* cited by examiner

BIOPRINTER SPRAY HEAD ASSEMBLY AND BIOPRINTER

RELATED APPLICATIONS

This Application is a national stage filing under 35 U.S.C. § 371 of International Patent Application Serial No. PCT/CN2015/099806, filed Dec. 30, 2015, the content of which is incorporated herein by reference in its entirety.

FIELD OF THE DISCLOSURE

The present disclosure relates to the field of bioprinting, and especially relates to a bioprinter spray head assembly and a bioprinter.

BACKGROUND OF THE DISCLOSURE

3D Biological printing refers to the printing of biological materials (including natural materials and synthetic materials or cellular solutions) into a designed three-dimensional structure through the principles and methods of 3D printing, which is different from 3D printing technology. The biological tissues or organs produced by 3D biological printing technology also have certain biological functions and need to provide conditions for the further growth of cells and tissues. Exactly due to the aforementioned characteristics, the 3D biological printing technology is confronted with many specific technical problems in development.

Among them, in the field of 3D biological printing, the technique of taking cells as a printing material is referred to as cell three-dimensional printing technology. People may utilize cells and biocompatible materials to make bio-ink. The nozzle moves and sprays the bio-ink, and the movement of the spray head is controlled by a program to print the bio-ink. The bio-ink is printed according to a three-dimensionally constructed digital model of a preset target print object.

The spray head for bioprinting in the prior art is similar to a nozzle of a syringe needle, which is mounted directly on the bioprinter. The spray head device of such bioprinter has a simple structure, is mainly used to fill active cells into a stent material, but cannot be wrapped before printing. Furthermore, in the process of directly spraying cells to the printing platform through a spray head, the extrusion pressure and the frictional force of the sidewalls of the nozzle over the cells may cause the cells in the bio-ink to be greatly damaged, so that an adverse effect may be produced over the survival rate of the cells, to further affect the construction of a biological construct.

SUMMARY OF THE DISCLOSURE

In order to overcome the above technical defects, the technical problem solved by the present disclosure is to provide a bioprinter spray head assembly and a bioprinter for printing a plurality of printing materials at the same time. Further, a plurality of printing materials may also be combined together before printing. For example, the first material as the bio-ink is preferably wrapped using the second material, so that it also has the advantage of protecting the cells in the sprayed bio-ink from damage as much as possible.

In order to solve the aforementioned technical problems, the first aspect of the present disclosure provides the technical solution that the spray head assembly is provided with a first flow channel and a second flow channel internally, wherein an outlet of the first flow channel is adjacent to an outlet of the second flow channel, and the outlet of the second flow channel is configured to make a second material sprayed therefrom move towards a direction of a first material sprayed from the outlet of the first flow channel, such that the second material sprayed from the outlet of the second flow channel and the first material sprayed from the outlet of the first flow channel are combined together to form a fluid printing unit.

In such technical solution, the second flow channel can direct and gradually converge the second material towards the direction of the first material, so as to combine the second material and the first material together. For example, the second material may be made to wrap the first material so as to form a fluid printing unit of a biological printing material to protect the cells, thereby reducing the cell damage caused by the extrusion pressure and the frictional force subjected in the printing process.

Further, the second flow channel is at least partially tapered along a direction towards its outlet.

In the improved technical solution, the second flow channel is at least partially tapered, to enable that the pressure of the second material is increased to raise its flow velocity, such that the second material flows more smoothly within the second flow channel, so as to better wrap the first material at the outlet of the first flow channel.

Further, the second flow channel is tapered adjacent to the outlet of the first flow channel.

In the improved technical solution, the second flow channel is tapered adjacent to the outlet of the first flow channel, so that a pressure can be applied to the second material along a direction towards the first material at a position adjacent to the outlet, to guide the second material to be sprayed towards a direction of the first material, so as to better wrap the first material.

Further, the second flow channel has a conical section adjacent to the outlet of the first flow channel and taken along a direction towards its outlet.

In the improved technical solution, the section of the second flow channel adjacent to the outlet of the first flow channel is conical, which has a better guiding effect over the second material and enables the same flow velocity of the second material at the same height. Therefore, the flow velocity arriving at the outlet of the second flow channel is also becoming same substantially, so as to effectuate that the second material covers the first material uniformly.

Further, the second flow channel and the first flow channel are gradually close to each other adjacent to respective outlets.

Further, the bioprinter spray head assembly comprises a spray head body and an extension rod, wherein the first flow channel communicates with an outlet of the spray head body, the extension rod is provided adjacent to the outlet of the spray head body, an open recess is provided on an end face of the extension rod adjacent to the spray head body, the outlet of the spray head body protrudes into the open recess, and an annular space between an outer wall of the spray head body and an inner wall of the open recess serves as the second flow channel.

In the technical solution of the first embodiment, by providing a tapered open recess on the end face of the extension rod adjacent to the spray head body, a encapsulation cavity is formed between the outlet of the spray head body and the outlet of the open recess, the second material can enter into the encapsulation cavity through the second flow channel between the outer wall of the spray head body and the open recess, and the first material sprayed from the spray head body is wrapped so as to form fluid printing units which flows within the open recess. The open recess is favorable for the convergence of the mixed fluid and ensures a more stable flow direction of the mixed fluid within the encapsulation cavity.

Further, an inclination of the inner wall of the open recess is greater than that of the outer wall of the spray head body.

In an improved technical solution of the first embodiment, the inclination of the inner wall of the open recess is greater than that of the outer wall of the spray head body, so that a tapered second flow channel can be formed between the outer wall of the spray head body adjacent to the first flow channel and the inner wall of the open recess, so as to realize a better wrapping effect.

Further, at the outlet of the second flow channel, the inner wall of the open recess is lower than the outer wall of the spray head body.

In an improved technical solution of the first embodiment, the inner wall of the open recess is lower than the outer wall of the spray head body, so that the extension portion formed by the open recess can be further tapered along a direction toward the outlet of the first flow channel, so as to guide the second material to further converge towards the first material, to facilitate wrapping the first material more adequately.

Further, the bioprinter spray head assembly comprises an outer nozzle having a first channel and an inner nozzle having a second channel, wherein the inner nozzle is provided within the first channel, and the second channel forms the first flow channel, and an annular space between an inner wall of the outer nozzle and an outer wall of the inner nozzle serves as the second flow channel.

In the technical solution of the second embodiment, by using the two-layer nozzle structure having inner and outer layers, the second material may be continuously guided to converge to the first material in the spraying process, so that the first material is wrapped at the outlet of the nozzle, thereby avoiding the first material from being damaged due to the effect of the mechanical frictional force when sprayed from the outlet of the nozzle.

Further, at the outlet of the second flow channel, the inner wall of the outer nozzle is lower than the outer wall of the inner nozzle.

In an improved technical solution of the second embodiment, the inner wall of the outer nozzle is lower than the outer wall of the inner nozzle, so that the extension portion of the outer nozzle can be further tapered along a direction toward the outlet of the first flow channel, so as to guide the second material to further converge towards the first material, to facilitate more reliably and wrapping the first material adequately.

Further, an inclination of the inner wall of the outer nozzle is greater than that of the outer wall of the inner nozzle.

In an improved technical solution of the second embodiment, the inclination of the inner wall of the outer nozzle is greater than that of the outer wall of the inner nozzle, to enable that the second flow channel is tapered adjacent to the outlet of the first flow channel along a direction towards the outlet of the first flow channel, to guide the second material to further converge to the center in the spraying process, so as to better realize the wrapping.

In order to solve the aforementioned technical problem, the second aspect of the present disclosure provides a bioprinter, comprising the bioprinter spray head assembly according to the aforementioned embodiments.

In the basic technical solution, the bioprinter can make the produced various biological constructs maintain a high activity and a long service life by obtaining a high-quality biological printing material.

Accordingly, based on the aforementioned technical solution, the present disclosure provides a bioprinter spray head assembly, which provides a first flow channel and a second flow channel, and makes an outlet of the first flow channel adjacent to an outlet of the second flow channel, and the outlet of the second flow channel is configured to make a second material sprayed therefrom move towards the first material, to enable that the second material sprayed from the outlet of the second flow channel wraps the first material sprayed from the outlet of the first flow channel, to form fluid printing units of biological printing material to protect the cells, thereby reducing the cell damage caused by the extrusion pressure and the frictional force subjected in the printing process, so as to improve the survival rate and reliability of the cells.

BRIEF DESCRIPTION OF THE ACCOMPANYING DRAWINGS

The drawings described herein are used to provide a further understanding of the present disclosure and constitute a part of the present application. The illustrative embodiments of the present disclosure as well as the descriptions thereof, which are merely used for explaining the present disclosure, do not constitute improper definitions on the present disclosure. In the drawings.

DETAILED DESCRIPTION OF THE PREFERRED EMBODIMENTS

Figure 1:
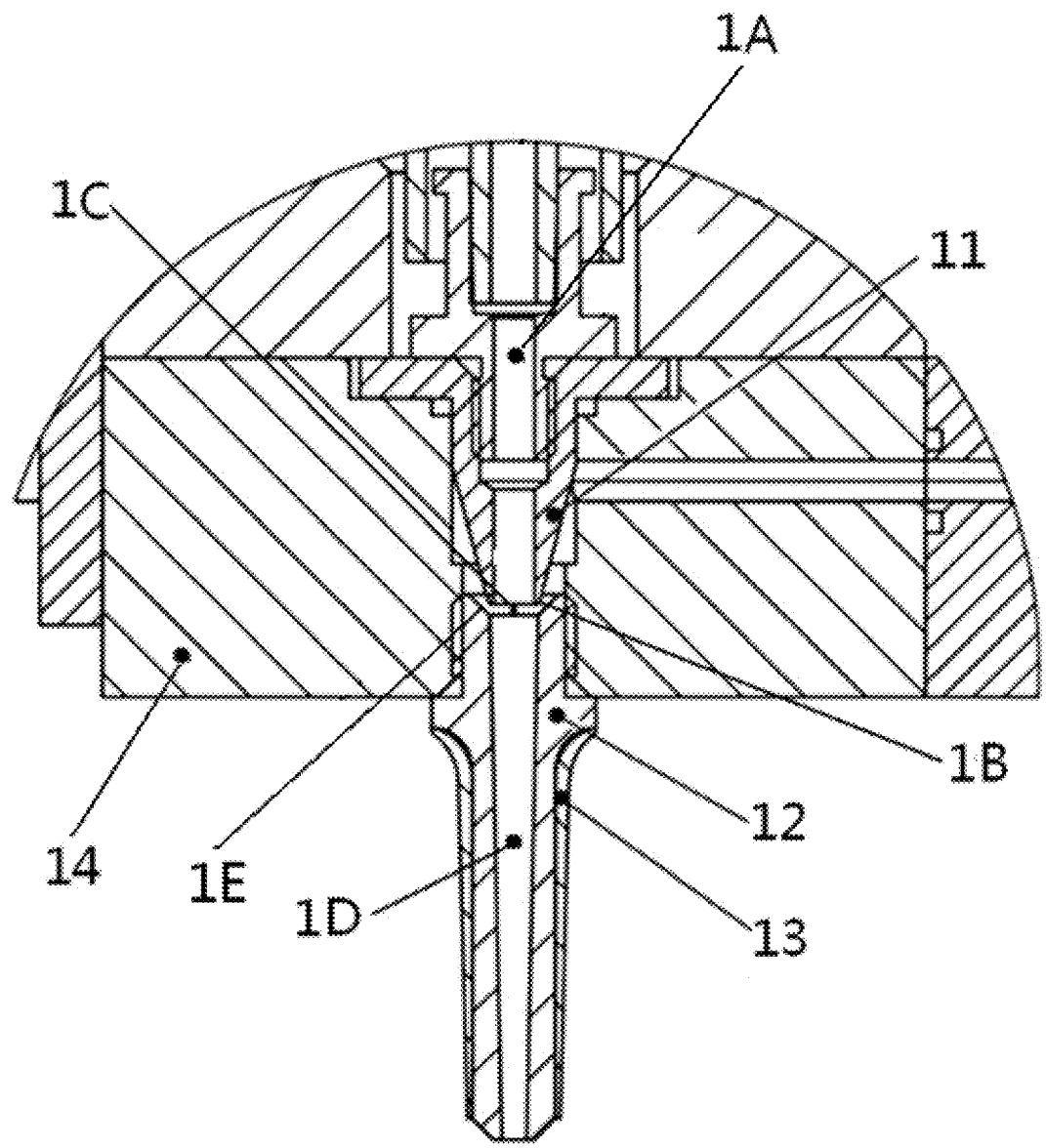
FIG. 1 is a schematic view of the structure of a first embodiment of the bioprinter spray head assembly of the present disclosure.

Next, the technical solution of the present disclosure is further described in detail by means of the drawings and embodiments.

The specific embodiments of the present disclosure are further described in order to facilitate understanding of the concept of the present disclosure, the technical problem to be solved, the technical features constituting the technical solution and the technical effect produced therefrom. It is necessary to explain that, the explanations for such embodiments do not constitute definitions on the present disclosure. In addition, the technical features involved in the embodiments of the present disclosure described below may be combined with each other as long as they do not constitute a conflict there between.

Considering that the spray head assembly of the bioprinter cannot wrap the cells before printing in the prior art, the cells maybe damaged in the printing process. Therefore, the present disclosure provides a bioprinter spray head assembly, and its structure and principles may refer to the embodiments shown in FIGS. 1 and 2. In one illustrative embodiment, the spray head assembly is internally provided with a first flow channel and a second flow channel which may transport the same kind of biological printing material, and may also be used for different kinds of biological printing materials. In addition, the first flow channel and the second flow channel may be used at the same time, and may also be used independent from each other.

When the first flow channel and the second flow channel are respectively used for two kinds of materials at the same time, the first flow channel serves as a flow channel for the first material used for the biological printing material (main material), and the second flow channel serves as a flow channel for the second material (auxiliary material) wrapping the biological printing material. The first flow channel is designated by the reference sign 1A in FIG. 1, and the reference sign 2A in FIG. 2, and the second flow channel is designated by the reference sign 1B in FIG. 1, and the reference sign 2B in FIG. 2. Furthermore, the outlet of the first flow channel is adjacent to the outlet of the second flow channel, and the outlet of the second flow channel is configured to make the auxiliary material sprayed therefrom move towards a movement direction of the main material, such that the auxiliary material sprayed from the outlet of the second flow channel is combined together with the main material sprayed from the outlet of the first flow channel to form a fluid printing unit. The combination manner may be mixing, wrapping or fusion. For example, the auxiliary material wraps the main material.

The fluid printing unit is a printing unit composed of a biological printing material, for example, a mixed fluid printing unit is formed by wrapping a main material with an auxiliary material. Regarding the main material and the auxiliary material, in a most preferred embodiment, the main material is a printing material containing cells, and the auxiliary material is a printing material that does not contain cells. In some embodiments, the auxiliary material is a material with temperature-sensitive properties, especially a biocompatible material with temperature-sensitive properties and certain viscosity, for example substances such as hydrogels. In other embodiments, the main material is a printing material that does not contain cells, while the auxiliary material is a printing material that contains cells. In the rest embodiments, the main material and the auxiliary material may also be printing materials that both contain cells, or may also be printing materials that do not contain cells. Regarding the morphology of the main material and the auxiliary material, either or both of them are one of the following several morphologies: homogeneous, non-homogeneous (e.g., granular mixture), continuous or discontinuous fluid.

According to the usage requirements, the auxiliary material may be a nutrient-supplying substance, may also be a substance for supplying an adhesive force (which may also be used for forming a protective layer), and may also provide a substance wrapped around the main material to form a protective layer.

The bioprinter spray head assembly of the embodiment, which changes the manner of directly printing the cells in the prior art, and which provides a first flow channel and a second flow channel, and makes the outlet of the first flow channel adjacent to an outlet of the second flow channel, and the outlet of the second flow channel configured to make the auxiliary material sprayed therefrom move towards a movement direction of the main material, and guide the auxiliary material to flow towards a movement direction of the main material over the entire circumference, and use a fluid focus principle to enable that the auxiliary material sprayed from the outlet of the second flow channel wraps the main material sprayed from the outlet of the first flow channel, to form a fluid printing unit so as to protect the cells, thereby reducing the cell damage caused by an external force such as an extrusion pressure applied by the air and the like and a frictional force rendered by the inner wall of the nozzle subjected in the printing process, so as to improve the survival rate and reliability of the cells.

In order to realize that the auxiliary material sprayed from the second flow channel is directed toward the main material, the second flow channel and the first flow channel may be gradually close to each other adjacent to the respective outlets, and it may be specifically realized by the following two structural forms, but not limited to this.

In the first structural form, the inner wall and the outer wall of the second flow channel adjacent to the outlet towards the movement direction of the main material are both tapered and parallel to each other. Optionally, the second flow channel is isodiametric, and at the outlet, the second flow channel extends obliquely towards the first flow channel, so that the second material in the second flow channel convergently moves towards the first fluid out of the first flow channel.

In the second structural form, the second flow channel is at least partially tapered, and such structure can increase the pressure of the auxiliary material, to raise the flow velocity, such that the auxiliary material flows more smoothly within the second flow channel, so as to wrap the main material at the outlet of the first flow channel better.

As a further improvement to the second structural form, the second flow channel is tapered adjacent to the outlet of the first flow channel along a direction towards the outlet of the first flow channel. This embodiment can apply the pressure to the auxiliary material along a direction towards the main material to guide the auxiliary material to be sprayed toward the main material, so as to better wrap the main material; and can also increase the pressure of the auxiliary material to raise the flow velocity, so that the auxiliary material flows out more smoothly to achieve the wrapping. Those skilled in the art may design a tapered degree of the second flow channel to achieve a controlled wrapping before printing.

In some embodiments, the second flow channel may be coaxially wrapped outside the first flow channel, and the second flow channel and the first flow channel are spaced apart from each other. The coaxial arrangement form is conducive to making the main material more uniformly wrapped outside the auxiliary material, and avoiding the phenomenon of uneven thickness as much as possible, so as to improve the quality of the fluid printing units.

In some embodiments, the second flow channel has a conical section adjacent to the outlet of the first flow channel and taken along a direction towards its outlet. For example, in the embodiment shown in FIG. 1, the inner wall and the outer wall of the second flow channel are both in an inverted conical shape, and the taper of the inner wall of the second flow channel is smaller than the corresponding taper of the outer wall. In the embodiment shown in FIG. 2, the inner wall of the second flow channel is cylindrical and the outer wall is in an inverted conical shape. The conical shape is easily machined, and the second flow channel designed in a conical shape presents a better guiding effect over the fluid than in other shapes, and may also enable that the auxiliary material has the same flow velocity at the same height, and enable that the flow velocities arriving at the outlet of the second flow channel are substantially the same, to further effectuate that the auxiliary material uniformly wraps the main material.

Two types of embodiments that can form a wrap-type fluid printing unit will be given below.

In the first embodiment, as shown in the structural schematic view of FIG. 1, the bioprinter spray head assembly comprises a spray head body 11 and an extension rod 12. The extension rod 12 is provided adjacent to the outlet of the spray head body 11. The extension rod 12 is internally provided with an elongated flow channel 1D for allowing that the fluid printing unit is orientedly sprayed through the flow channel 1D. By providing an elongated flow channel 1D in the extension rod 12, the fluid printing unit can be orientedly guided and sequenced to reduce the possibility of obstruction. Moreover, the fluid printing units can also be protected in the spraying process, to reduce the damage of the mechanical force over the fluid printing unit in the printing process, so as to improve the reliability of the fluid printing units. Further, a thermal insulation element 13 may also be provided on the outer periphery of the extension rod 12. The thermal insulation element 13 can ensure that the fluid printing unit maintains a desired temperature in the flow channel 1D to maintain the activity of the fluid printing units, so as to overcome the technical problem in the prior art that the nozzle without an extension rod has to extend certain length to facilitate the application of the sprayed material so that it is inconvenient for thermal insulation. For the time being, there is no prior art found to wrap an entirety of the spray head with a thermal insulation element in the field of biological 3D bioprinting. Moreover, as the main material (biological printing material) and the auxiliary material (eg.hydrogel) are very sensitive to the temperature, there are strict temperature control demands in the field of 3D printing, that are not necessary to other technical fields.

For the mounting forms of various components in this embodiment, we may refer to FIG. 1. The extension rod 12 is located immediately below the spray head body 11. The spray head body 11 and the extension rod 12 may be coaxially provided within the mounting part 14. In an expanded form, the extension rod 12 may be directly mounted on the spray head body 11 without providing the mounting part 14.

More specifically, an open recess 1E is provided on the end face of the extension rod 12 adjacent to the spray head body 11, and the outlet of the open recess 1E communicates with the flow channel 1D. The spray head body 11 extends into the open recess 1E. The channel provided inside the spray head body 11 serves as the first flow channel 1A, and the annular space between the outer wall of the spray head body 11 and the inner wall of the open recess 1E serves as the second flow channel 1B. Also, a encapsulation cavity 1C is formed between the outlet of the first flow channel 1A and the outlet of the open recess 1E, and the auxiliary material sprayed from the outlet of the second flow channel 1B wraps the main material sprayed from the outlet of the first flow channel 1A in the encapsulation cavity 1C, so as to form a fluid printing unit. The fluid printing unit flows within the open recess 1E, by utilizing the flow focus principle, the main material after being gradually wrapped by the auxiliary material is discharged from the cavity into the flow channel 1D. The open recess 1E facilitates convergently mixing the fluid, and ensures a more stable flow direction of the fluid printing unit within the encapsulation cavity 1C.

In this embodiment, the inner wall of the open recess 1E has an inclination greater than that of the outer wall of the spray head body 11, so that a tapered second flow channel can be formed between the outer wall of the spray head body adjacent to the first flow channel and the inner wall of the open recess, so as to make the wrapping effect better.

For example, in the first structure, the outer wall of the spray head body 11 and the inner wall of the open recess 1E are both in an inverted conical shape, and the taper of the outer wall of the spray head body 11 is smaller than that of the inner wall of the open recess 1E, enabling the auxiliary material to flow along the annular space between the conical surfaces of the spray head body 11 and the open recess 1E, which produces a favorable guiding effect and is favorable for uniformly wrapping the main material by the auxiliary material. In the second structure, the outer wall of the spray head body 11 is cylindrical, and the inner wall of the open recess 1E is in an inverted conical shape, so that it may also effectuate tapering to produce the converging effect.

For the aforementioned first embodiment and improved solution, the main material and the auxiliary material may be wrapped at the outlet of the corresponding flow channel. In some embodiments, at the outlet of the second flow channel 1B, the inner wall of the open recess 1E is lower than the outer wall of the spray head body 11, so that the outlet of the second flow channel 1B may be lower than the outlet of the first flow channel 1A, and the extension portion formed by the open recess 1E can be further tapered along a direction towards the outlet of the first flow channel 1A to guide the auxiliary material to further converge towards the main material, so as to more reliably and adequately wrap the main material. For a specific structure, if the outer wall of the spray head body 11 is conical, while the inner wall of the open recess 1E is in an inverted conical shape, the outlet of the second flow channel 1B needs to be lower than the outlet of the first flow channel 1A so as to guide the auxiliary material to converge towards the main material.

The operational principles of such bioprinter spray head assembly according to the present disclosure will be described below in combination with the first embodiment shown in FIG. 1. The main material after being sprayed from the spray head body 11 enters the encapsulation cavity 1C, the auxiliary material enters the encapsulation cavity 1C through the second flow channel 1B formed between the outer wall of the spray head body 11 and the inner wall of the open recess 1E. The auxiliary material in the encapsulation cavity 1C has certain pressure. The size of the pressure may adjust a thickness of a wrapping layer of the auxiliary material, and oppress the auxiliary material attach to the main material exposed from the spray head body 11, after an entirety of the main material is sprayed, the auxiliary material fully wraps the main material, which finally allows that the main material continuously wrapped by the auxiliary material enters the flow channel 1D of the extension rod 12. The main material wrapped by the auxiliary material orientedly flows within the elongated flow channel 1D, and at the same time is uniformly wrapped and sequentially discharged.

In the second embodiment, as shown in the structural schematic view of FIG. 2, the bioprinter spray head assembly comprises an outer nozzle 21 having a first channel and an inner nozzle 22 having a second channel, wherein the inner nozzle 22 is provided within the first channel, and the second channel forms the first flow channel 2A, and an annular space between an inner wall of the outer nozzle 21 and an outer wall of the inner nozzle 22 serves as the second flow channel 2B.

In some embodiments, the inner wall of the outer nozzle 21 has an inclination greater than that of the outer wall of the inner nozzle 22, so that the second flow channel 2B may be tapered adjacent to the outlet of the first flow channel 2A, and may guide the auxiliary material to further converge towards the center in the spraying process, to wrap the main material at the outlet of the inner nozzle 22 so as to avoid that the main material is damaged when sprayed from the outlet due to a mechanical frictional force as much as possible. As can be seen from FIG. 2, the outer wall of the inner nozzle 22 adjacent to the outlet is cylindrical, and the inner wall of the outer nozzle 21 adjacent to the outlet is conical, so as to effectuate that the second flow channel 2B is tapered adjacent to the outlet. In addition, the outer wall of the inner nozzle 22 adjacent to the outlet may also be conical, and it is necessary to satisfy that the taper of the outer wall of the inner nozzle 22 adjacent to the outlet is less than that of the inner wall of the outer nozzle 21.

In some embodiments, the outer nozzle 21 and the inner nozzle 22 are coaxially disposed to form a concentric double-layered structural pattern, so that the second flow channel may more uniformly wrap the main material.

In general, at the outlet of the second flow channel 2B, the inner wall of the outer nozzle 21 and the outer wall of the inner nozzle 22 may be designed in a flush manner. More preferably, at the outlet of the second flow channel 2B, the inner wall of the outer nozzle 21 is lower than the outer wall of the inner nozzle 22, so that the extension portion of the outer nozzle 21 can be further tapered along a direction toward the outlet of the first flow channel 2A, so as to guide the auxiliary material to further converge towards the main material, to facilitate more reliably and adequately wrapping the main material.

Figure 2:
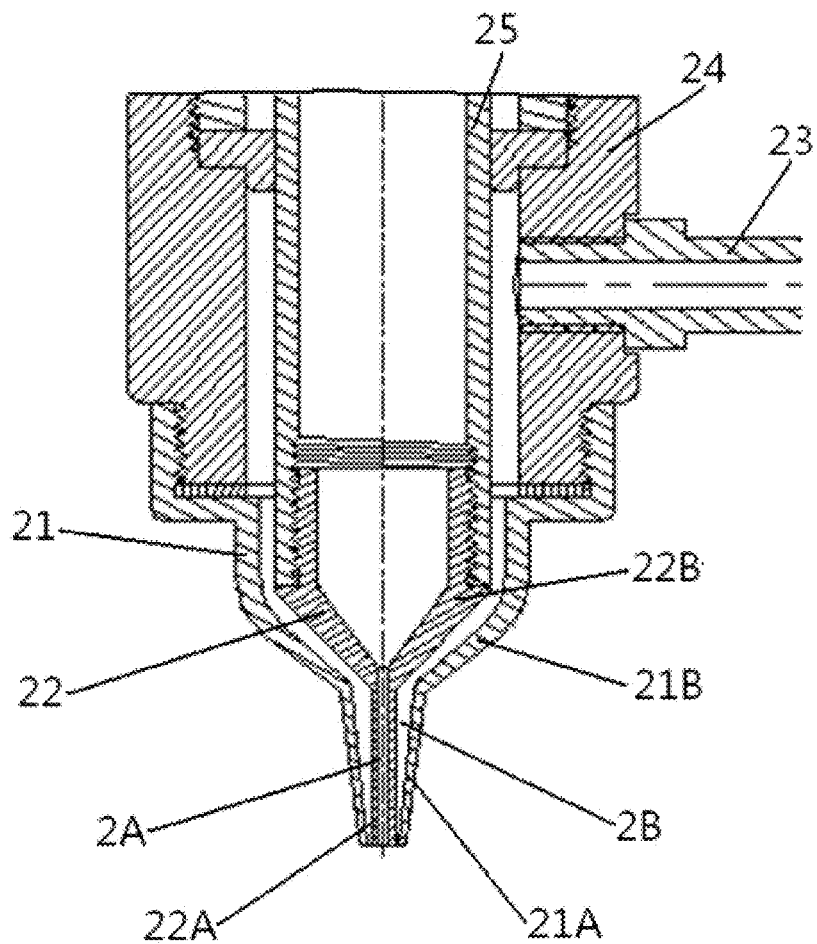
FIG. 2 is a schematic view of the structure of a second embodiment of the bioprinter spray head assembly of the present disclosure.
Figure 3:
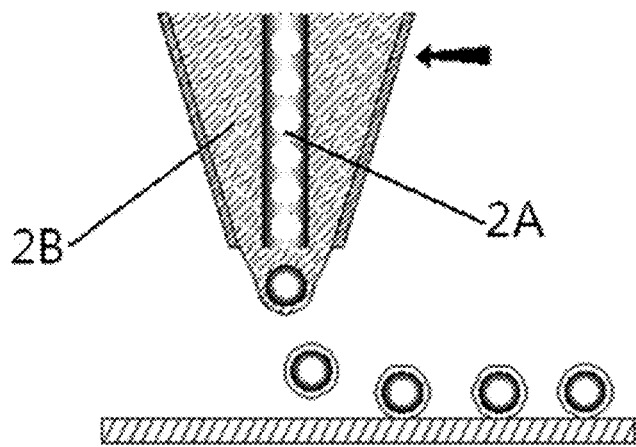
FIG. 3 is a schematic view of a state of the fluid printing unit flowing out in the second embodiment shown in FIG. 2.

A specific implementation structure is given below, as shown in FIG. 2, the outer nozzle 21 includes a first guide portion 21A and a first body portion 21B. The inner nozzle 22 includes a second guide portion 22A and a second body portion 22B. The first guide portion 21A and the second guide portion 22A are provided adjacent to the outlets of the corresponding nozzles, and the annular space between the first guide portion 21A and the second guide portion 22A is tapered along a direction toward the outlet of the nozzle. In addition, the corresponding cross-section of the first flow channel 2A at the first guide portion 21A is a cylindrical flow channel, and it is best to enable channel of a single row of main materials (for example, a cellular ink unit), to guide the main material to be more smoothly sprayed and wrapped by the auxiliary material, so as to form a granular biological printing material that meets the printing requirements.

In the specific structural form, the first body portion 21B includes a first cylindrical portion and a first conical portion. The first conical portion is connected between the first guide portion 21A and the first cylindrical portion, and the first cylindrical portion is connected with a outer nozzle connecting body 24 by threaded fit or in other fastening manners. The outer nozzle connecting body 24 is provided with a connection tube 23 for introducing the auxiliary material into the second flow channel 2B. The second body portion 22B includes a second cylindrical portion and a second conical portion. The second conical portion is connected between the second guide portion 22A and the second cylindrical portion. The second cylindrical portion is connected with a main material circulation tube 25 by threaded fit or in other fastening manners. Wherein, the second conical portion produces a transitional effect, to reduce the cross-sectional area of the first flow channel 2A, so that the main material is converted into a fluid printing unit that meets the printing requirements when flowing out. The first conical portion is designated to be adapted to the second conical portion so as to produce a guiding effect over the auxiliary material.

As a more preferable embodiment, the second flow channel 2B is tapered between the first conical portion and the second conical portion so that the pressure of the auxiliary material is increased, and the flow velocity is increased. The reason lies in that, according to the formula for the flow rate of the spout of the nozzle $Q=\mu*A*(\Delta P/\rho)^{0.5}$, Q is a flow rate, μ is a coefficient, A is a cross-sectional area of the spout, ΔP is a pressure difference, and ρ is a liquid density. At the same time, Q=vA, wherein v is a flow velocity. When the pressure intensity of a material container is certain, the flow rate is certain. Then, the parameters that vary within the flow channel are respectively: a cross-sectional area, a pressure intensity difference and a flow rate. The relations between them can be roughly understood in a way such that: there is a greater pressure intensity and a faster flow velocity when the cross-section is reduced. Therefore, there are relative high pressure areas and low pressure areas appearing at local locations within the flow channel. The flow velocity of the high pressure area is greater than that of the low pressure area, but the flow rate is changeless.

In summary, by reducing the cross-section here, the pressure intensity is increased and the flow velocity is accelerated. As a result, the auxiliary material which flows more smoothly within the second flow channel 2B, is less likely to be obstructed, and wraps the main material more adequately at the outlet.

The operational principles of such spray head assembly according to the present disclosure will be described in detail below in combination with the second embodiment shown in FIG. 2. Under the control of the pressure, the main material flows along the first flow channel 2A, and the auxiliary material flows along the tapered second flow channel 2B. The auxiliary material has certain pressure to be attached to the main material arriving at the outlet of the first flow channel 2A when arrives at the outlet of the second flow channel 2B, to gradually effectuate that it is fully wrapped to form a fluid printing unit, and sequentially sprayed from the outlet of the spray head assembly.

For the aforementioned embodiments of both types, it is necessary to realize flow of a biological printing material by means of pressure control, for example air pressure control. A main material container and a auxiliary material container when filled up with materials are respectively connected with the electrical proportional valve in the air path. The respective corresponding electrical proportional valves of the two containers are then communicated with the control system in real-time analog amount, and the extrusion amount of the two containers are respectively controlled via the instructions issued by the upper software. The spraying velocity of the fluid within the first flow channel and the second flow channel may be controlled by respectively adjusting the air pressure.

Different control manners may be adopted according to different printing demands. When it is necessary to form a continuous biological printing material, it is possible to add the main material within the main material container, and add the auxiliary material within the auxiliary material container. By applying a constant air pressure, the main material may be continuously sprayed, and externally wrapped by the auxiliary material to integrally form an elongated structure. As shown in FIG. 3, when it is necessary to form a granular biological printing material, it is possible to add the main material within the main material container, and add the auxiliary material within the auxiliary material container. Pulses are formed by frequent pressurization and opening and closing actions. The main material forms particles under the effect of the pulses, and is combined with the outer layer of auxiliary material to form a structure similar to egg yolk and egg white, which is rapidly cooled and molded under the effect of temperature.

In addition, the present disclosure also provides a bioprinter, which comprises the above-described bioprinter spray head assembly. Since the bioprinter spray head assembly of the present disclosure can wrap the cells during printing so that the cells are protected from damage and present a high survival rate, the bioprinter using such spray head assembly also possesses the corresponding advantageous technical effects, and can enable the produced various biological constructs to maintain a high activity and a long service life by obtaining a high-quality biological printing material. Preferably, the bioprinter is a biological 3D bioprinter, and the bioprinter spray head assembly of the present disclosure is especially suitable for a biological 3D bioprinter.

The above introduces in detail a bioprinter spray head assembly and bioprinter provided by the present disclosure. Specific embodiments are applied in this text to elaborate the principles and embodiments of the present disclosure, and the aforementioned descriptions of the embodiments are only used to help understanding the method of the present disclosure as well as its core thoughts. It should be set forth that, for a person skilled in the art, on the premise of not departing away from the principles of the present disclosure, several modifications and decorations may also be made to the present disclosure, and such modifications and decorations also fall into the protection scope of the claims of the present disclosure.

The invention claimed is:

1. A bioprinter spray head assembly, comprising a first flow channel and a second flow channel, an outlet of the first flow channel is adjacent to an outlet of the second flow channel, and the outlet of the second flow channel is configured to make a second material sprayed therefrom move towards a first material from the outlet of the first flow channel, such that the second material sprayed from the outlet of the second flow channel and the first material sprayed from the outlet of the first flow channel are combined together to form a fluid printing unit; wherein the bioprinter spray head assembly comprises a spray head body and an extension rod, the first flow channel communicates with an outlet of the spray head body, the extension rod is provided adjacent to the outlet of the spray head body, an open recess is provided on an end face of the extension rod adjacent to the spray head body, the outlet of the spray head body protrudes into the open recess, and an annular space between an outer wall of the spray head body and an inner wall of the open recess serves as the second flow channel, and the second flow channel is at least partially tapered along a direction towards its outlet.

2. The bioprinter spray head assembly according to claim 1, wherein the second flow channel is tapered adjacent to the outlet of the first flow channel.

3. The bioprinter spray head assembly according to claim 2, wherein the second flow channel has a conical section adjacent to the outlet of the first flow channel and taken along a direction towards the outlet of the first flow channel.

4. The bioprinter spray head assembly according to claim 1, wherein the second flow channel and the first flow channel are gradually close to each other adjacent to respective outlets.

5. The bioprinter spray head assembly according to claim 1, wherein an inclination of the inner wall of the open recess is greater than that of the outer wall of the spray head body.

6. The bioprinter spray head assembly according to claim 1, wherein at the outlet of the second flow channel, the inner wall of the open recess is lower than the outer wall of the spray head body.

7. A bioprinter, comprising the bioprinter spray head assembly according to claim 1.

* * * * *